US012714333B2

(12) United States Patent
De Laat

(10) Patent No.: US 12,714,333 B2
(45) Date of Patent: Aug. 25, 2026

(54) VAGINAL MEASUREMENTS USING A VAGINAL RING

(71) Applicant: LiGalli B.V., The Hague (NL)

(72) Inventor: Wilhelmus Nicolaas Gerardus Maria De Laat, The Hague (NL)

(73) Assignee: LiGalli B.V., The Hague (NL)

( * ) Notice: Subject to any disclaimer, the term of this patent is extended or adjusted under 35 U.S.C. 154(b) by 0 days.

(21) Appl. No.: 16/970,183

(22) PCT Filed: Apr. 10, 2019

(86) PCT No.: PCT/EP2019/059127

§ 371 (c)(1),
(2) Date: Aug. 14, 2020

(87) PCT Pub. No.: WO2019/197486

PCT Pub. Date: Oct. 17, 2019

(65) Prior Publication Data

US 2021/0113120 A1 Apr. 22, 2021

(30) Foreign Application Priority Data

Apr. 10, 2018 (EP) .................................... 18166628
Sep. 12, 2018 (EP) .................................... 18194033
Sep. 12, 2018 (EP) .................................... 18194034

(51) Int. Cl.
*A61B 5/00* (2006.01)
*A61B 5/11* (2006.01)
*A61B 5/145* (2006.01)

(52) U.S. Cl.
CPC ........ *A61B 5/14503* (2013.01); *A61B 5/1107* (2013.01); *A61B 5/1451* (2013.01);
(Continued)

(58) Field of Classification Search
CPC . A61B 5/14503; A61B 5/1107; A61B 5/1451; A61B 5/14532; A61B 5/14539;
(Continued)

(56) References Cited

U.S. PATENT DOCUMENTS

2002/0010414 A1* 1/2002 Coston .................. A61N 1/325
604/20
2003/0004403 A1* 1/2003 Drinan .................. G16H 40/67
977/925

(Continued)

FOREIGN PATENT DOCUMENTS

JP 2018509389 4/2018
WO WO2016120402 A1 8/2016

(Continued)

*Primary Examiner* — Alex M Valvis
*Assistant Examiner* — Grace L Rozanski
(74) *Attorney, Agent, or Firm* — Mandar A. Joshi; Peter W. Schroen; Bret E. Field

(57) ABSTRACT

Method for measuring the presence of a compound or a physiological parameter in the human or animal body, comprising positioning an intravaginal ring that comprises a sensor for the compound or parameter to be measured in contact with the vaginal mucosa and recording a signal produced by the sensor. It is further disclosed a method for the combined administration and measurement of compounds in the human or animal body, comprising the administration of one or more biologically active compounds and the simultaneous and/or subsequent measurement of the presence and/or concentration of the same and/or another compound and/or physiological parameter that is the result of the administration of the one or more biologically active compounds, wherein the measurement is performed with a sensor that is in contact with the vaginal mucosa.

4 Claims, 7 Drawing Sheets

Figure 1:
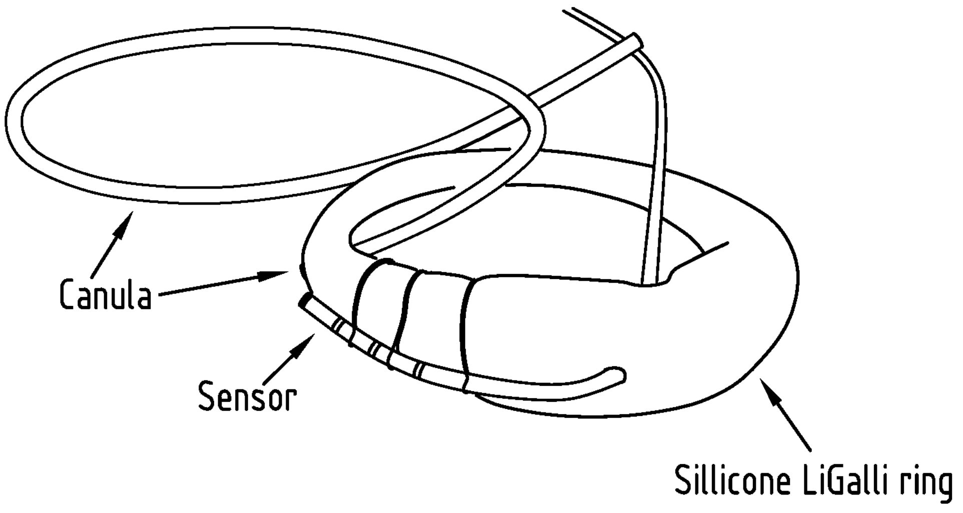

(52) U.S. Cl.
CPC ...... *A61B 5/14532* (2013.01); *A61B 5/14539* (2013.01); *A61B 5/14546* (2013.01); *A61B 5/4294* (2013.01); *A61B 5/4839* (2013.01); *A61B 5/6847* (2013.01); *A61B 2503/40* (2013.01)

(58) Field of Classification Search
CPC . A61B 5/14546; A61B 5/4294; A61B 5/4839; A61B 5/6847; A61B 2503/40
See application file for complete search history.

(56) References Cited

U.S. PATENT DOCUMENTS

| | | | | |
|---|---|---|---|---|
| 2006/0084848 | A1 | 4/2006 | Mitchnick | |
| 2009/0004246 | A1* | 1/2009 | Woolfson | C07K 16/1063 424/430 |
| 2013/0211372 | A1* | 8/2013 | Rosenshein | A61B 5/6846 702/19 |
| 2013/0225922 | A1* | 8/2013 | Schentag | A61B 1/0684 600/109 |
| 2016/0022198 | A1* | 1/2016 | De Laat | A61M 5/1723 604/285 |
| 2016/0045158 | A1* | 2/2016 | Hsu | A61B 5/14532 600/347 |
| 2016/0143630 | A1* | 5/2016 | Pardey | A61B 5/01 600/549 |
| 2017/0079587 | A1 | 3/2017 | Fougere et al. | |
| 2017/0181669 | A1* | 6/2017 | Lin | G01N 33/66 |
| 2017/0197068 | A1* | 7/2017 | Erhard | A61M 5/14276 |
| 2018/0369391 | A1* | 12/2018 | Onorato | C08J 9/286 |
| 2019/0160332 | A1* | 5/2019 | Beer | A61B 5/486 |

FOREIGN PATENT DOCUMENTS

| | | | |
|---|---|---|---|
| WO | WO2017060299 | A1 | 4/2017 |
| WO | WO2018023037 | A1 | 2/2018 |

* cited by examiner

VAGINAL MEASUREMENTS USING A VAGINAL RING

The present invention relates to a method for measuring the presence of a compound or physiological parameter in the human or animal body.

For diagnostic and therapeutic purposes it may be relevant to be able to determine the presence of particular compounds in the human or animal body, such as in samples of blood, plasma, urine, feces, semen, or in breath or on the skin etc. For all these samples, different techniques are used. Some of these techniques are invasive such as the withdrawal of blood.

Diabetic patients do for example use lancets or automated finger-pricking devices that pierce the skin so that a drop of blood can be extracted for testing. Although such self-monitoring of blood glucose at home is already a huge improvement over having to go to a hospital for extracting blood, it may still be considered a burden by the patient. Frequent pricking causes pain and the compliance may not be optimal.

A way to measure glucose levels in real-time throughout the day and night is Continuous Glucose measurement (CGM). A tiny glucose sensor is inserted under the skin to measure glucose levels in the interstitial fluid in the subcutaneous fat tissue. It is connected to a transmitter that sends the information to a monitoring device. The sensor of the CGM is to be inserted through the skin by means of a needle, which is invasive and is certainly not painless. Other sensors need to be inserted through the skin after a surgical intervention.

In the research that led to the present invention it was found that the vaginal mucosal wall, which is situated just above a very dense microcirculation area, easily allows a pass through of biochemical data (like glucose) and many other compounds (like LH and estradiol) that can be measured by a sensor in contact with this wall. Sensors that are positioned against the vaginal wall, for example via an intravaginal ring do not need surgical intervention and can be positioned by the patient herself. The procedure is non-invasive.

The research leading to the invention was initially performed on glucose. There is no report in the medical literature that the vaginal wall transudate contains glucose. The present inventors for the first time established by direct sampling from a healthy volunteer that the vaginal wall transudate contains 4-6 mmol/L glucose. The next question was whether this glucose level reflects the levels of glucose found in capillary blood and interstitial fluid and fluctuations in blood glucose.

In order to investigate this, the results of glucose monitoring via CGM, finger-pricking and a glucose sensor mounted to an intravaginal ring were compared. It was found that an intravaginal device, comprising an intravaginal ring and a glucose sensor was able to measure stable and repeatable signals from the vaginal wall. Results revealed that similar patterns of the obtained vaginal and blood glucose could be observed, indicating a correlation between the vaginal and blood glucose. The results obtained with the vaginal wall transudate glucose monitoring fulfilled the criteria for clinical use, as all values were within zone A of a Consensus Error Grid, which is used as a reference for CGM.

It was furthermore found that also luteinizing hormone (LH) and estradiol (E2) could be measured in the vaginal transudate.

The invention thus relates to a method for measuring the presence of a compound in the human or animal body, comprising positioning an intravaginal ring that comprises a sensor for the compound to be measured in contact with the vaginal mucosa and recording a signal produced by the sensor. The intravaginal ring is suitably in close contact with the vaginal wall transudate. The advantage of the use of an intravaginal ring is that the device is invisible for the outside world and does not hinder the wearer like external devices with wiring would do.

Diagnostic vaginal rings are known in the prior art but only for temperature-monitoring. Such rings comprise temperature loggers embedded in silicone elastomer. It is not known to measure compounds in the vaginal mucosa or transudate.

Figure 5:
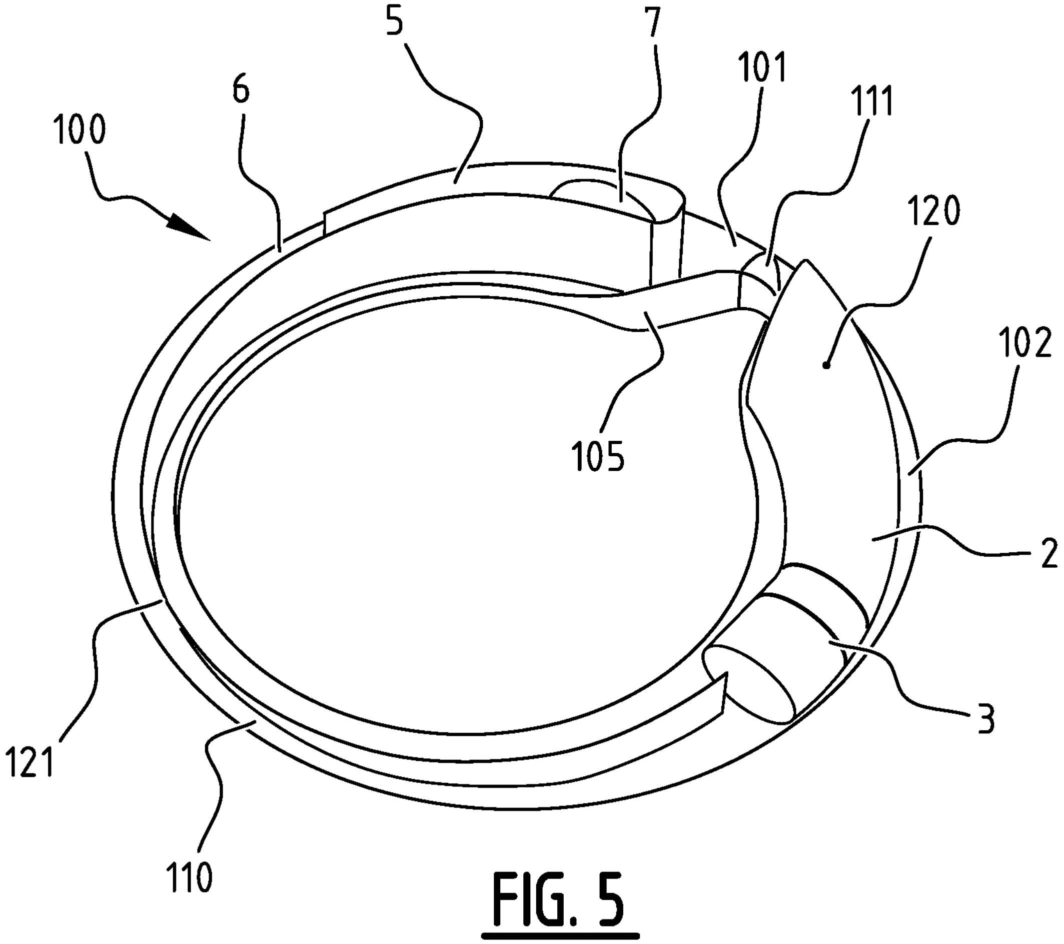

The present invention can be very well performed by using an intravaginal ring as disclosed in WO2017/060299. The ring is large enough to contain both a battery and electronic equipment to control and process the sensor. It is thus a stand-alone device that can function without external components, except for an external device that receives the data transmitted from the sensor, for example by means of an antenna. The intravaginal diagnostic device is thus invisible from the outside and does not need additional devices in, on, or in front of the body, like a transmitter or monitoring device. The data are suitably directly transmitted to a smartphone app. The configuration of the ring without the sensor is shown in FIG. 5.

The transvaginal ring can have two functions, one to measure one or more compounds for diagnostic purposes and the other to release a therapeutic compound for treatment purposes. Both functions can be combined in one device. The measurements of the compound can be used to control the release of a therapeutic agent from a reservoir that is also part of the vaginal ring.

For the diagnostic function the ring should in any case comprise a sensor for measuring a compound or other parameter of interest. In addition, means for transmitting the measured data are to be present. For the therapeutic function the device should contain a reservoir or container to hold the therapeutic compound, a pump to release the therapeutic compound and means for controlling the release. Such control means can for example interact with the measuring means to determine the release profile of the therapeutic compound.

The position of the sensor in the ring is preferably close to the vaginal vascular bed. In FIG. 5 this position corresponds with reference numerals 101 and 102. This way exchange of compounds between the vasculature and the vaginal transudate is optimal, which leads to a more accurate measurement.

In a preferred embodiment, the sensor is in contact with a smartphone app. The app shows the results of the measurements and can be used to monitor the development of the concentration of the compound. The release function of the ring can also be controlled via the app.

The present invention can be used for the measurement of all compounds that are present in the vaginal transudate. The invention is in particular useful for determining the presence of glucose, lactate, estradiol, progesterone, luteinizing hormone (LH), follicle stimulating hormone (FSH), androstenedion, cortisol, tiiododothyonine (T3), thyroxine (T4), iodothyramine (T1a), thyronamine (T0a), melatonine, testosterone, dehydroepiandrosterone, troponine, cytokines, etc. In addition, other physiological parameters can be measured with this device, such as pH, muscular activity like bladder contractions, pelvic floor muscular status, motility, etc.

The invention is useful to register over time the measurements allowing an individual data profile which can be of value for monitoring the patients condition and adjust medication or life style.

If equipped with a lab-on-a-chip, the diagnostic ring will be capable of measuring simultaneously the results of drug delivery of medical compounds by measuring the diagnostic result derivatives of such drug administration (like glucose measurement after insulin/glucagon administration, estradiol after FSH or pulsed GnRH administration, progesterone after HCG, prolactin after bromocryptine, or medication levels after drug delivery of such medications, like antidepressants and antipsychotics, known for their non-compliant intake, where a vaginal ring achieves 100% compliance.

For each compound a separate sensor or a separate sensor function needs to be present. In one embodiment different sensors can be combined in one vaginal ring. Different sensor functions can also be combined in one sensor.

The invention further relates to a method for determining the blood glucose and/or interstitial fluid glucose value in an individual, comprising performing a method for measuring the presence of a compound in the human or animal body, comprising positioning a vaginal ring that comprises a sensor for the compound to be measured in contact with the vaginal mucosa and recording a signal produced by the sensor and correlating the value obtained from the sensor with a reference to determine the corresponding blood glucose and/or interstitial fluid glucose value.

The invention further provides a method for the combined administration and measurement of compounds in the human or animal body, comprising the administration of one or more biologically active compounds and the simultaneous and/or subsequent measurement of the presence and/or concentration of the same and/or another compound and/or physiological parameter that is the result of the administration of the one or more biologically active compounds, wherein the measurement is performed with a sensor that is in contact with the vaginal mucosa.

Suitably, the sensor is comprised in an intravaginal ring and the administration of the one or more biologically active compounds is also performed by the intravaginal ring.

In one embodiment, FSH or pulsed GnRH is administered and estradiol or estradiol/LH is measured. In another embodiment, LH or HCG is administered and progesterone is measured. In a further embodiment insulin or glucagon is administered and glucose is measured.

This method is also suitable for measuring an antidepressant or antipsychotic drug that is administered by intravaginal ring to the patient.

The present invention will be further illustrated in the Examples that follows and that is intended for illustration purposes and is not in any way limiting to the invention.

In the Examples reference is made to the following figures:

FIG. 1: Combined catheter- and ring device comprising a glucose sensor. The catheter was coated with NovioSense coating and was fixed on the ring with surgical steel fixing material.

FIG. 2: Glucose in vagina vs blood glucose.

Figure 3A:
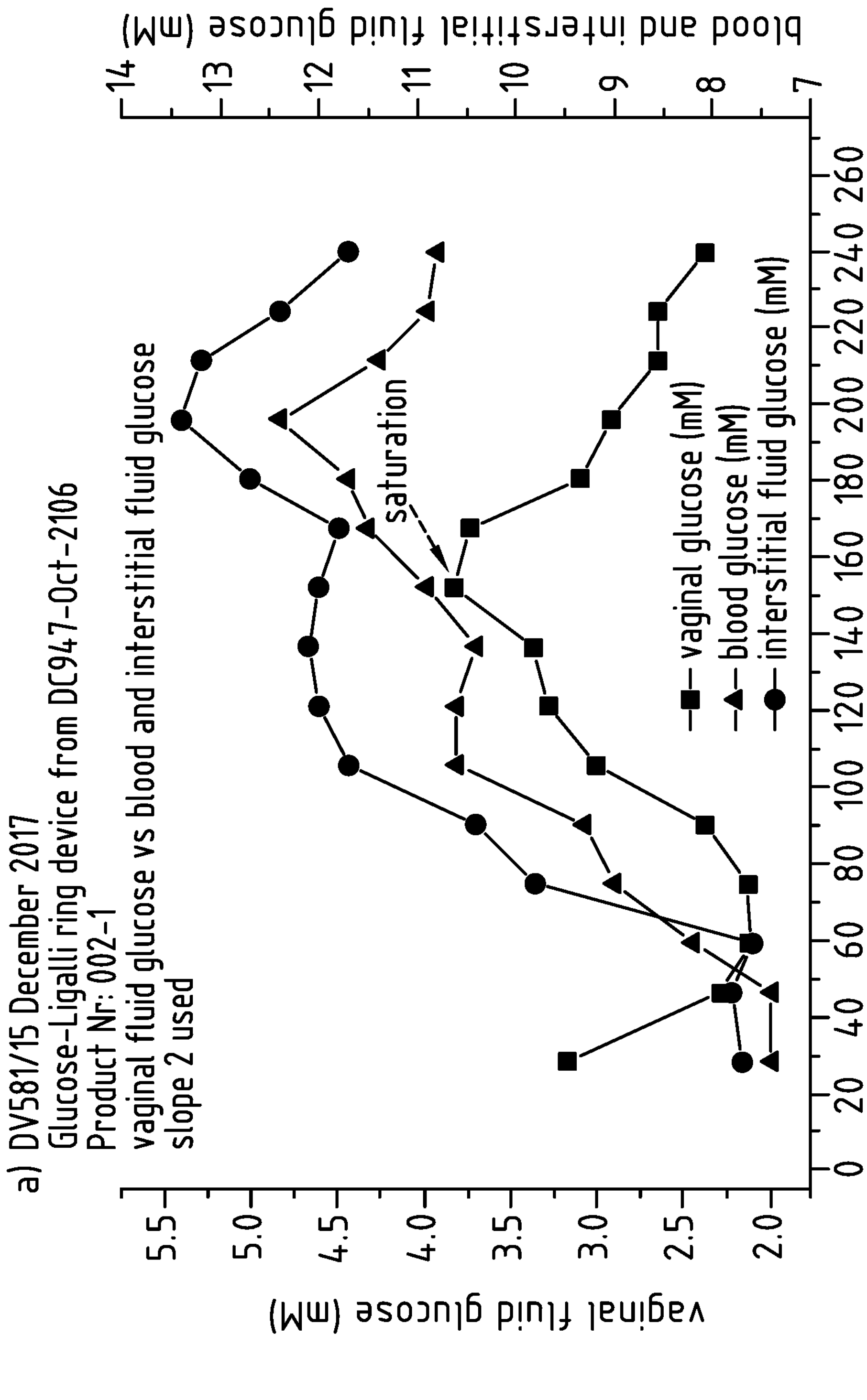
Figure 3B:
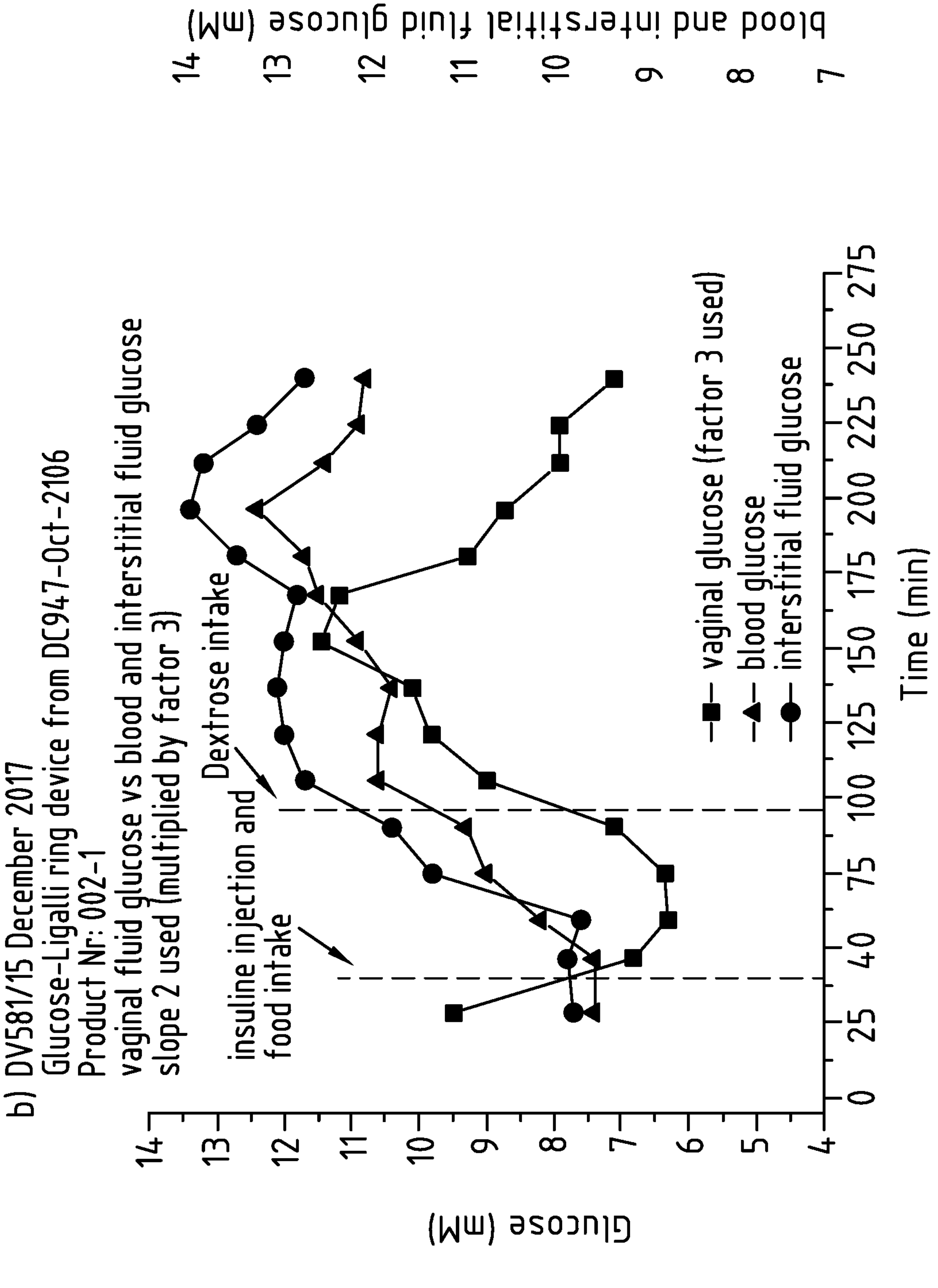

FIG. 3: Glucose in vagina vs blood glucose and interstitial fluid glucose.

Figure 4:
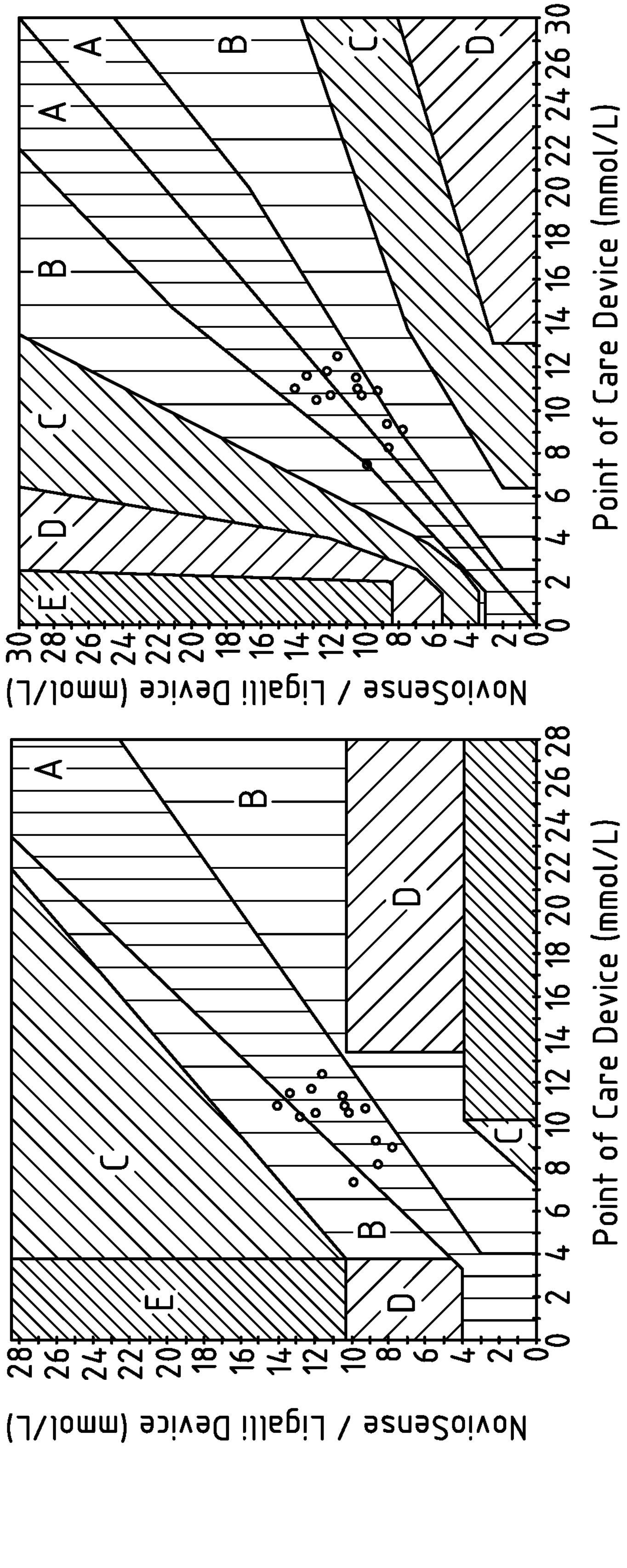

FIG. 4: Clarke Error Grid (left) and Consensus Error Grid (right) collected from intravaginal LiGalli/NovioSense device in pilot clinical trial.

FIG. 5: Schematic representation of an intravaginal ring device.

EXAMPLES

Example 1

Determination of Glucose in Vaginal Transudate in a Healthy Volunteer

Introduction

This pilot study was performed to investigate if a glucose sensor can measure a shift in glucose concentration, when flushed intravaginally near the sensor with bolus solution. Moreover, it was important to see if glucose can be measured in the vagina when the device is placed in contact with the vaginal wall.

The glucose sensor-ring device thus obtained was placed in the vagina in contact with the vaginal wall of a healthy female volunteer aged 43 years for an approximately 1 hour 20 min (71 min) period. The capillary blood glucose level was obtained from a finger stick glucose test, the commercially available Bayer glucose meter. Blood sugar was tested three times in this pilot study. Glucose bolus solutions (5 mM, 10 mM and 20 mM) were flushed in the vagina through a cannula (2 mL per bolus).

Materials and Methods

The device was coated with NovioSense coating and was mounted and fixed with surgical steel material on a silicone intravaginal ring from LiGalli. After coating and/or assembly the functionalized device was stored in the fridge.

The coating and assembly of the device was carried out in a clean room.

The different glucose concentration solutions were prepared by mixing 20 mM glucose solution with saline solution (0.9% NaCl solution). The following proportions of solutions were mixed to get the required glucose concentration solution.

Results

This trial was conducted with a healthy women volunteer, age 43 years old. The catheter-LiGalli ring device was firstly calibrated at glucose solution range 0-10 mM. After calibration, the device was inserted in vagina by a gynecologist in a correct position so that the sensor was in contact with the vaginal wall.

The first signals of the sensor were recorded just after insertion. In parallel, blood glucose value was recorded. The stable, linear trends of the signals was observed.

Afterwards, 2 mL of 0.9% saline solution was flushed through the cannula and the signal registration was recorded.

Subsequently, two dextrose tablets were consumed by the volunteer and after waiting approximately 10 min, the registration of the signal by glucose sensor-ring device was monitored again. In parallel the capillary blood glucose value was recorded.

After the consumption of dextrose as requested by the clinician and waiting for 10 min to record the measurement, no increase in a signal could be observed in the vagina.

Therefore, it was decided to start the '2nd test' in order to see if the device can measure a shift in glucose concentration, when flushed intravaginally near the sensor with 2 mL of 5 mM, 10 mM and 20 mM glucose bolus solutions.

The measured current had an increase at 5 mM and 10 mM glucose concentrations. However, no increase at 20 mM glucose could be observed. The reason for this is most likely that at this concentration the saturation level of substrate was reached with the higher glucose concentration. Thus, 20 mM glucose concentration was too high to use for the measurement. Still, it can be concluded that device can measure a shift in glucose because the sensor had an instant response to increasing glucose concentrations.

Figure 2A:
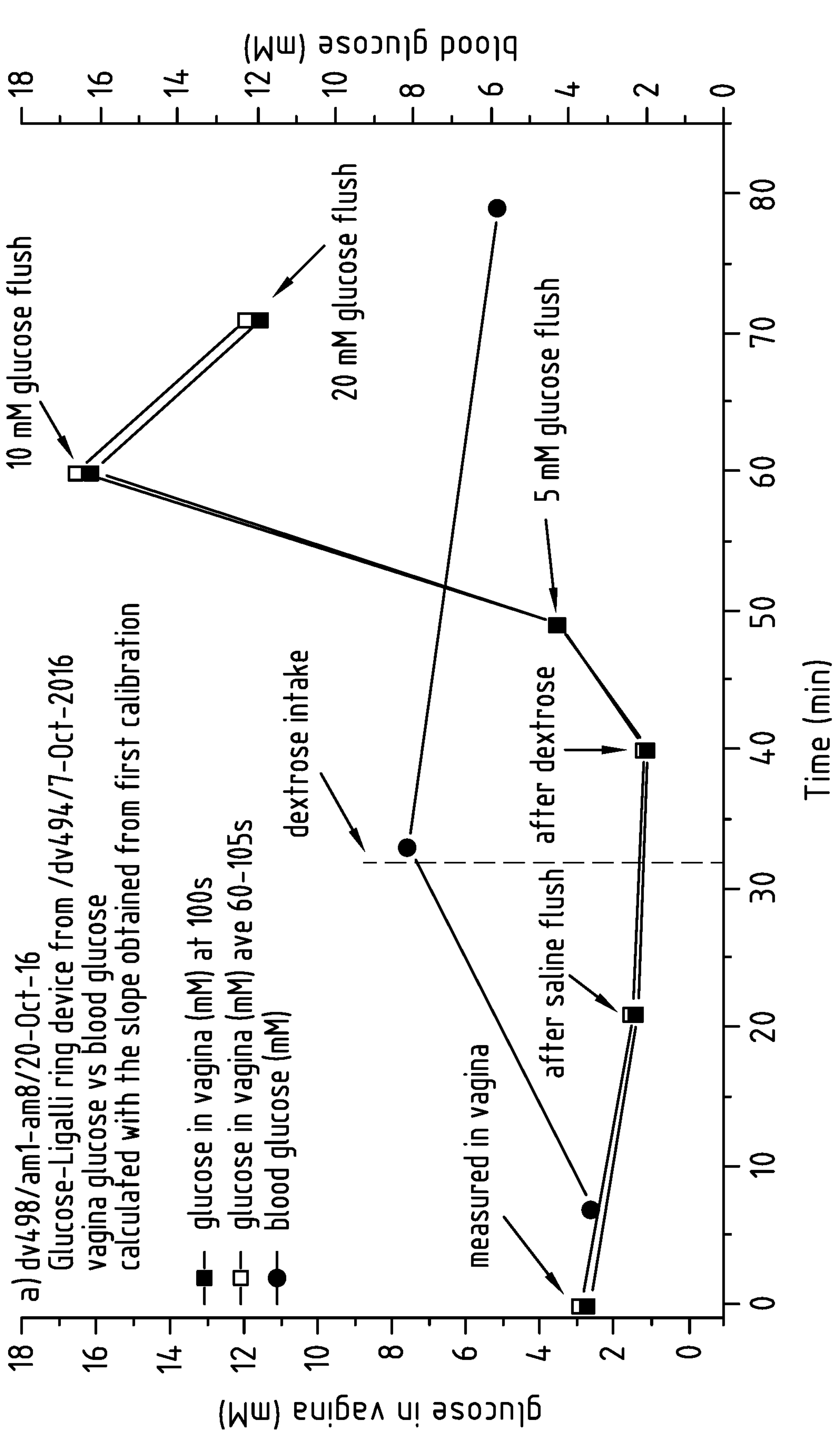
Figure 2B:
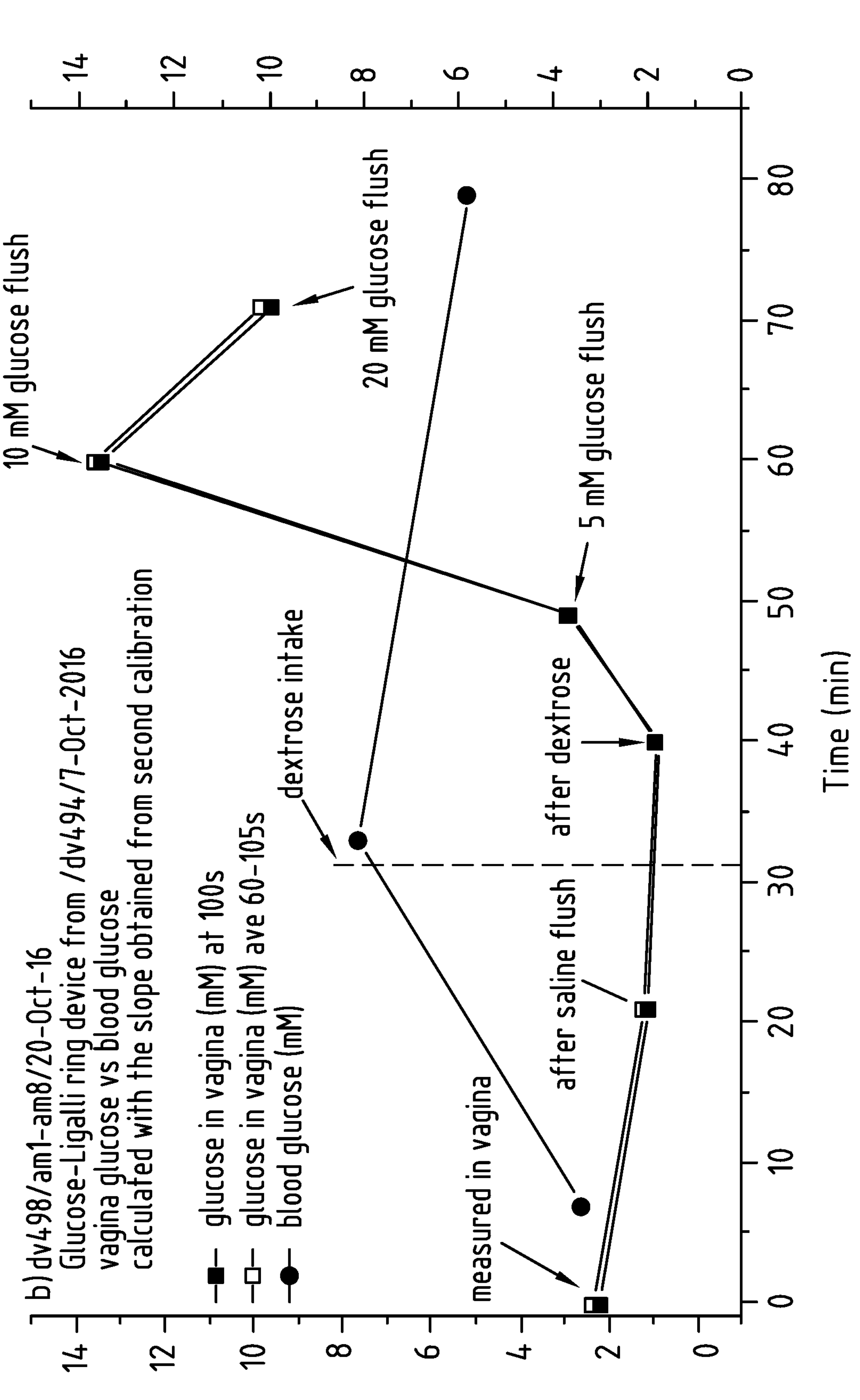

The device signal response in vagina versus blood glucose is plotted. The signal of the device gradually decreased up to 40 min, until 5 mM and 10 mM glucose bolus solutions were flushed, however the average signals were relatively stable. While, the measured blood glucose value had increased, however there is no data available relating to the lag time between blood and vaginal secretion. FIGS. 2*a* and 2*b* depicts the data. However, the obtained current values were recalculated in this case using data obtained from the calibration measurements. It should be noted that two slopes were obtained, firstly from the initial sensor calibration and secondly the slope used for recalculation after measurement in the vagina.

From the acquired data it seems, that the first measured glucose values in vagina and in capillary blood are almost same.

As it was mentioned the catheter-LiGalli ring device was calibrated twice: before device insertion and after removal from vagina. The calibration curves were obtained at glucose range 0-10 mM.

Conclusion

The in vivo pilot work demonstrated that the glucose sensor-ring device can function and give a stable and clear response in vagina. Since, an instant response of the sensor to increasing glucose concentration (at 5 mM and 10 mM) was observed, it can be concluded that device can measure a shift in a glucose concentration.

Example 2

Determination of Glucose in Vaginal Transudate in a Diabetic Patient

Introduction

This aim of this example was to investigate the ability and efficacy of an intravaginal device to measure glucose in transudate proximal to the vaginal wall. In addition, the study was conducted to investigate if glucose sampled from vaginal wall transudate reflects levels of glucose found in capillary blood and interstitial fluid.

The intravaginal device used is a combination of an intravaginal ring as disclosed in WO2017/060299 (LiGalli) and the glucose sensor technology described in EP2699690 (NovioSense). The ring and measuring sensor are placed directly against the vaginal wall in a flexible manner and do not penetrate tissue itself, thus the device is formally non-invasive in its classification.

A diagnostic catheter was retrofitted and coated with a NovioSense coating followed by mounting on a LiGalli ring device (FIG. 1). The ring device thus obtained was placed in the vagina in contact with vaginal wall of a female volunteer aged 23 years, diagnosed with insulin dependent diabetes mellitus (type I) for a 4 hours (240 min) period. The device was pre-calibrated prior to insertion in the vagina.

The subject also had a CGM device (Abbot FreeStyle Libre) to measure glucose values from interstitial fluid. The capillary blood was obtained from a finger stick glucose test, measured with a glucose meter. Blood and interstitial fluid sugars were tested every 15 minutes. The current measured with the glucose sensor was detected approximately every 3 min.

Materials and Methods

The coating and assembly of the device was carried out in a clean room.

The catheter-LiGalli ring device was assembled as follows. The catheter coated with NovioSense coating and was mounted and fixed with surgical steel material on a silicone intravaginal ring from LiGalli. After coating and/or assembly the functionalized device was stored in the fridge.

Calibration was carried out at a 0-10 mM glucose concentration range. A 20 mM glucose solution was prepared from 20% glucose solution diluted with saline solution. The different glucose concentration solutions were prepared by mixing the 20 mM glucose solution with saline solution (0.9% NaCl solution).

Results and Discussion

This trial was conducted with a female volunteer, age 23 years old with diagnosed insulin dependent diabetes mellitus (type I). After calibration, the device was inserted in the vagina by a gynecologist in a correct position so that the sensor had a good contact with the vaginal wall. In parallel, capillary blood glucose and interstitial glucose values were monitored every 15 min.

It was found that stable signals could be recorded using the intravaginal device.

After 30 min measurement, the patient administered insulin and consumed the lunch. A continuous increase in the measured blood and interstitial fluid glucose was observed after 45 min and 60 min, respectively, while a gradual raise in the current response of the vaginal sensor was detected from 75 min. After 98 min of the commencement of the measurements, the patient consumed six dextrose tablets. As a consequence, all three devices exhibited gradual increase in the measured values until an apparent peak was reached. After the attained peak, the trends drop continuously.

The current measured with the intravaginal device was recorded more frequently (every 3 min) in comparison with the monitored blood and interstitial fluid glucose.

All three graphs show similar patterns. However, the peaks were reach at different time points. Which indicates that there might be a delay between the blood glucose, interstitial fluid and vaginal fluid glucose.

It could be observed that up to approximately 180 min current measured with the intravaginal device has a similar pattern as the blood glucose detected by finger prick. Most likely there is a delay between the blood and vaginal fluid glucose between 30 to 50 min. There might be a delay between the interstitial fluid glucose and vaginal fluid glucose of around 15 min.

The obtained current values were recalculated. FIG. 3*a* shows vaginal glucose detected by intravaginal device vs blood glucose and interstitial fluid glucose.

From the acquired data it seems, that vaginal wall glucose has a similar continuous increase when compared to the blood and interstitial fluid glucose. The peak for vaginal fluid glucose was reached at around 120 min, where the blood glucose measured value was equal to 10.9 mM.

A Clarke Error grid was plotted to determine the ability of the intravaginal sensor to measure blood glucose values. A Clarke error grid is a graphical method to illustrate and calculate the accuracy of a sensor regarding clinical decisions. Values obtained from a sensor are plotted against the blood glucose acquired from a Point of Care device which is known to be a golden standard. The graph used for the Clark error grid is divided into different areas and assigned a letter from A-E. Points falling within A and B areas are considered as valid measurements which mean that a treatment decision i.e. to administer insulin or not based on that value is a correct decision. Data points falling in the C, D and E region are considered to lead to invalid or incorrect treatment decision with varying levels of potential harm to the patient with C being a wrong decision with low risk to the patient and E being of high risk. The Clarke error grid and Consensus Error Grid produced in the pilot trial is shown in FIG. 4.

The international requirement for accuracy at the time the data were collected was collected was derived from ISO 15197:2003 which stated that to be considered clinically acceptable 95% of data should fall within the A or B regions. Both error grids shown in FIG. 4 confirm that the sensor had sufficient accuracy to be proceed to the next phase of development.

Conclusion

This Example shows that the intravaginal device was able to measure stable and repeatable signals in the vagina for up to 4.5 hours. It was noted that the glucose sensor when placed against the vaginal mucosal wall needs time to stabilize (around 30 min).

Results revealed that similar patterns of the obtained vaginal and blood glucose could be observed, indicating a correlation between the vaginal and blood glucose. The accuracy of the obtained data shown in both Clark Error Grid and Consensus Error Grid lay in the A and B region indicating high potential of the sensor to be further studied.

Example 3

Measurement of Estradiol and LH in Vaginal Transudate

A tiny swab was used to scrape along the vaginal mucosa. The swab was subsequently centrifuged and 1 μl sample fluid was retrieved. In order to measure the concentration of estradiol from this small volume a PBS solution was added and tested for the presence of estradiol. It was found that the sample contained 0.082 nmol/L. The sample was diluted 75-50×. Since the sample volume was extremely small and the dilution factor was high the obtained value may not be very accurate but it demonstrates in any case that estradiol can be measured from vaginal wall transudate In a similar manner, also LH (luteinizing hormone) was assayed. For this 1 μl of the sample was added to 199 μl PBS. The concentration of LH was 200×0.234=484 U/L. In the same sample the concentration of estradiol (E2) was 200×0.103=206 nmol/L. Here again are the same restrictions on the accuracy of the measurements with the used sample method.

This shows that also LH and estradiol can be determined in the vaginal transudate.

The concentrations of steroid hormones in vaginal wall transudate might be higher than plasma levels of the hormones and possibly even more representative for ovarian function than plasma levels. A 5-10 fold higher estradiol concentration was measured in vaginal tissue compared to plasma (Wiegerinck M A et al., J Clin Endocrinol Metab. 56(1):76-86 (1983)).

The invention claimed is:

1. A method for continuously determining a circulating blood glucose value, the method comprising:

positioning an intravaginal ring that comprises a sensor for continuously measuring the glucose-value in the vaginal wall transudate;

continuously recording a signal produced by the sensor; and continuously and simultaneously correlating the glucose value in the vaginal wall transudate as obtained from the signal produced by the sensor with a reference to continuously and simultaneously determine the corresponding circulating blood glucose value.

2. The method as claimed in claim 1, wherein the obtained values from the sensor are transmitted to an external device.

3. The method as claimed in claim 2, wherein the external device is a smartphone.

4. The method of claim 1, wherein the circulating blood glucose value is a capillary blood glucose value.

* * * * *